US007601358B2

(12) United States Patent
Fox et al.

(10) Patent No.: US 7,601,358 B2
(45) Date of Patent: Oct. 13, 2009

(54) MYCOBACTERIUM TUBERCULOSIS PROTEIN COMPOSITION

(75) Inventors: Brian G. Fox, Madison, WI (US); Yong Chang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/899,080

(22) Filed: Sep. 4, 2007

(65) Prior Publication Data

US 2008/0199869 A1 Aug. 21, 2008

Related U.S. Application Data

(60) Provisional application No. 60/841,822, filed on Sep. 1, 2006.

(51) Int. Cl.
*A61K 39/04* (2006.01)
*A61K 39/38* (2006.01)
*A61K 39/00* (2006.01)

(52) U.S. Cl. ............... 424/248.1; 424/184.1; 424/185.1; 424/243.1; 530/300; 530/350; 536/23.1; 536/23.7

(58) Field of Classification Search ............... 424/184.1, 424/185.1, 243.1, 248.1; 530/300, 350; 536/23.1, 536/23.7
See application file for complete search history.

(56) References Cited

U.S. PATENT DOCUMENTS

2005/0180963 A1* 8/2005 Adams et al. ............ 424/93.45

OTHER PUBLICATIONS

Ausubel et al., *Current Protocols in Molecular Biology*, vols. 1-4, John Wiley & Sons, Inc., New York, NY (1987-2004).
Bateman et al., "The Pfam protein families datebase," *Nucl. Acids Res.*, 32: D138-D141 (2004).
Dieffenbach et al., *PCR Primer: A Laboratory Manual*, Cold Spring Harbor Laboratory Press, Cold Spring Harbor, NY (1995).
Falvella et al., "Stearoyl-CoA desaturase 1 (*Scd1*) gene overexpression is associated with genetic predisposition to hepatocarcinogenesis in mice and rats," *Carcinog.* 23(11):1922-1936 (2002).
Kriegler, *Gene Transfer and Expression: A Laboratory Manual*, Stockton Press, New York, NY (1990).
Lu et al., "Gene Expression Changes Associated With Chemically Induced Rated Mammary Carcinogenesis," *J. Mol. Carcinog.*, 20:204-215 (1997).
Miyaji et al., "Expression of Human Lymphotoxin Derivatives in *Escherichia coli* and Comparison of Their Biological Activity in Vitro," *Agric. Biol. Chem.*, 53(1):277-279 (1989).
Ntambi et al., "Regulation of stearoyl-CoA desaturases and role in metabolism," *Prog. Lipid. Res.*, 43:91-104 (2003).
Pala et al., "Erythrocyte Membrane Fatty Acids and Subsequent Breast Cancer: a Prospective Italian Study," *J. Nat. Canc. Inst.*, 93(14):1088-1095 (2001).
Sambrook et al., 2000, *Molecular Cloning: A Laboratory Manual*, third edition, Cold Spring Harbor Laboratory Press, Cold Spring Harbor, NY.
Sambrook et al., 1989, *Molecular Cloning: A Laboratory Manual*, second edition, Cold Spring Harbor Laboratory Press, Cold Spring Harbor, NY.
Sekine et al., Cloning and expression of cDNA for salmon growth hormone in *Escherichia coli, Proc. Natl. Acad. Sci. USA.*, 82:4306-4310 (1985).
Yanisch-Perron et al., "Improved M13 phage cloning vectors and host strains: nucleotide sequences of the M13mp18 and pUC19 vectors," *Gene*, 33:103-119 (1985).
Whitney et al., "Functional characterisation of two cytochrome $b_5$-fusion desaturases from *Anemone leveillei*: the unexpected identification of a fatty acid $\Delta^6$-desaturase," *Planta*, 217:987-992 (2003).
International Search Report dated Sep. 23, 2008 for PCT Application No. PCT/US07/77423.

* cited by examiner

*Primary Examiner*—Rodney P. Swartz
(74) *Attorney, Agent, or Firm*—Brinks Hofer Gilson & Lione

(57) ABSTRACT

*Mycobacterium tuberculosis* proteins and protein compositions that are components of a desaturase complex are provided. The *Mycobacterium tuberculosis* desaturase complex may include a desaturase and an oxidoreductase. The complex may include the rv3229c and rv3230c gene products of *Mycobacterium tuberculosis*. Vectors for expressing the desaturase and the oxidoreductase can be packaged together, including a label that indicates their use as a complex for analyzing desaturation of fatty acids. In addition, methods for screening target ligands specific for a desaturase complex are also provided.

19 Claims, 2 Drawing Sheets

SEQUENCE LISTING

<160> NUMBER OF SEQ ID NOS: 10

<210> SEQ ID NO 1
<211> LENGTH: 41
<212> TYPE: DNA
<213> ORGANISM: Artificial

-continued

```
<220> FEATURE:
<223> OTHER INFORMATION: rv3230c primer 1

<400> SEQUENCE: 1
cggggtacca tcgagggaag gatgagcaag aaacacacga c                41

<210> SEQ ID NO 2
<211> LENGTH: 32
<212> TYPE: DNA
<213> ORGANISM: Artificial
<220> FEATURE:
<223> OTHER INFORMATION: rv3230c primer 2

<400> SEQUENCE: 2
cccaagcttc tagatgtcca gcacgcaatc ac                           32

<210> SEQ ID NO 3
<211> LENGTH: 41
<212> TYPE: DNA
<213> ORGANISM: Artificial
<220> FEATURE:
<223> OTHER INFORMATION: rv3229c primer 1

<400> SEQUENCE: 3
gggaattcca tatggcgatc actgacgtcg acgtattcgc g                 41

<210> SEQ ID NO 4
<211> LENGTH: 32
<212> TYPE: DNA
<213> ORGANISM: Artificial
<220> FEATURE:
<223> OTHER INFORMATION: rv3229c primer2

<400> SEQUENCE: 4
cccaagcttg gctgccagat cgtcgggttc gg                           32

<210> SEQ ID NO 5
<211> LENGTH: 36
<212> TYPE: DNA
<213> ORGANISM: Artificial
<220> FEATURE:
<223> OTHER INFORMATION: Gene-specific primer containing gene-specific
      overlap region plus portion of OLE1 starter sequence

<400> SEQUENCE: 5
ccaaaggatg actctgccag cagtggcatt gtcgac                       36

<210> SEQ ID NO 6
<211> LENGTH: 60
<212> TYPE: DNA
<213> ORGANISM: Artificial
<220> FEATURE:
<223> OTHER INFORMATION: Forward primer containing remainder of OLE1
      starter sequence

<400> SEQUENCE: 6
ccaacttctg gaactactat tgaattgatt gacgaccaat ttccaaagga tgactctgcc   60

<210> SEQ ID NO 7
<211> LENGTH: 59
<212> TYPE: DNA
<213> ORGANISM: Artificial
<220> FEATURE:
<223> OTHER INFORMATION: Forward primer containing ribosomal binding
      site and recombination site for Gateway cloning.

<400> SEQUENCE: 7
```

```
gggacaagt tgtacaaag caggctccaa taatgtctcc aacttctgga actactatt    59
```

<210> SEQ ID NO 8
<211> LENGTH: 30
<212> TYPE: DNA
<213> ORGANISM: Artificial
<220> FEATURE:
<223> OTHER INFORMATION: Reverse primer containing recombination site
      for Gateway cloning.

<400> SEQUENCE: 8

```
ggggaccact ttgtacaaga aagctgggtc                                  30
```

<210> SEQ ID NO 9
<211> LENGTH: 400
<212> TYPE: PRT
<213> ORGANISM: Mycobacterium tuberculosis

<400> SEQUENCE: 9

```
Met Arg Gly Ser His His His His His Gly Ser Ala Cys Glu Leu
1               5                   10                  15

Gly Thr Ile Glu Gly Arg Ser Lys Lys His Thr Thr Leu Asn Ala Ser
            20                  25                  30

Ile Ile Asp Thr Arg Arg Pro Thr Val Ala Gly Ala Asp Arg His Pro
35                  40                  45

Gly Trp His Ala Leu Arg Lys Ile Ala Ala Arg Ile Thr Thr Pro Leu
50                  55                  60

Leu Pro Asp Asp Tyr Leu His Leu Ala Asn Pro Leu Trp Ser Ala Arg
65                  70                  75                  80

Glu Arg Gly Arg Ile Leu Gly Val Arg Arg Glu Thr Glu Asp Ser Ala
            85                  90                  95

Thr Leu Phe Ile Lys Pro Gly Trp Gly Phe Ser Phe Asp Tyr Gln Pro
100                 105                 110

Gly Gln Tyr Ile Gly Ile Gly Leu Leu Val Asp Gly Arg Trp Arg Trp
115                 120                 125

Arg Ser Tyr Ser Leu Thr Ser Ser Pro Ala Ala Ser Gly Ser Ala Arg
130                 135                 140

Met Val Thr Val Thr Val Lys Ala Met Pro Glu Gly Phe Leu Ser Thr
145                 150                 155                 160

His Leu Val Ala Gly Val Lys Pro Gly Thr Ile Val Arg Leu Ala Ala
            165                 170                 175

Pro Gln Gly Asn Phe Val Leu Pro Asp Pro Ala Pro Pro Leu Ile Leu
180                 185                 190

Phe Leu Thr Ala Gly Ser Gly Ile Thr Pro Val Met Ser Met Leu Arg
195                 200                 205

Thr Leu Val Arg Arg Asn Gln Ile Thr Asp Val Val His Leu His Ser
210                 215                 220

Ala Pro Thr Ala Ala Asp Val Met Phe Gly Ala Glu Leu Ala Ala Leu
225                 230                 235                 240

Ala Ala Asp His Pro Gly Tyr Arg Leu Ser Val Arg Glu Thr Arg Ala
            245                 250                 255

Gln Gly Arg Leu Asp Leu Thr Arg Ile Gly Gln Gln Val Pro Asp Trp
260                 265                 270

Arg Glu Arg Gln Thr Trp Ala Cys Gly Pro Glu Gly Val Leu Asn Gln
275                 280                 285

Ala Asp Lys Val Trp Ser Ser Ala Gly Ala Ser Asp Arg Leu His Leu
```

```
                    290                 295                 300

Glu Arg Phe Ala Val Ser Lys Thr Ala Pro Ala Gly Ala Gly Gly Thr
305                 310                 315                 320

Val Thr Phe Ala Arg Ser Gly Lys Ser Val Ala Asp Ala Ala Thr
325                 330                 335

Ser Leu Met Asp Ala Gly Glu Gly Ala Gly Val Gln Leu Pro Phe Gly
340                 345                 350

Cys Arg Met Gly Ile Cys Gln Ser Cys Val Val Asp Leu Val Glu Gly
355                 360                 365

His Val Arg Asp Leu Arg Thr Gly Gln Arg His Glu Pro Gly Thr Arg
370                 375                 380

Val Gln Thr Cys Val Ser Ala Ala Ser Gly Asp Cys Val Leu Asp Ile
385                 390                 395                 400

<210> SEQ ID NO 10
<211> LENGTH: 435
<212> TYPE: PRT
<213> ORGANISM: Mycobacterium tuberculosis

<400> SEQUENCE: 10

Met Ala Ile Thr Asp Val Asp Val Phe Ala His Leu Thr Asp Ala Asp
1               5                   10                  15

Ile Glu Asn Leu Ala Ala Glu Leu Asp Ala Ile Arg Arg Asp Val Glu
            20                  25                  30

Glu Ser Arg Gly Glu Arg Asp Ala Arg Tyr Ile Arg Arg Thr Ile Ala
        35                  40                  45

Ala Gln Arg Ala Leu Glu Val Ser Gly Arg Leu Leu Leu Ala Gly Ser
    50                  55                  60

Ser Arg Arg Leu Ala Trp Trp Thr Gly Ala Leu Thr Leu Gly Val Ala
65                  70                  75                  80

Lys Ile Ile Glu Asn Met Glu Ile Gly His Asn Val Met His Gly Gln
                85                  90                  95

Trp Asp Trp Met Asn Asp Pro Glu Ile His Ser Ser Thr Trp Glu Trp
            100                 105                 110

Asp Met Ser Gly Ser Ser Lys His Trp Arg Tyr Thr His Asn Phe Val
        115                 120                 125

His His Lys Tyr Thr Asn Ile Leu Gly Met Asp Asp Asp Val Gly Tyr
    130                 135                 140

Gly Met Leu Arg Val Thr Arg Asp Gln Arg Trp Lys Arg Tyr Asn Ile
145                 150                 155                 160

Phe Asn Val Val Trp Asn Thr Ile Leu Ala Ile Gly Phe Glu Trp Gly
                165                 170                 175

Val Ala Leu Gln His Leu Glu Ile Gly Lys Ile Phe Lys Gly Arg Ala
            180                 185                 190

Asp Arg Glu Ala Ala Lys Thr Arg Leu Arg Glu Phe Ser Ala Lys Ala
        195                 200                 205

Gly Arg Gln Val Phe Lys Asp Tyr Val Ala Phe Pro Ala Leu Thr Ser
    210                 215                 220

Leu Ser Pro Gly Ala Thr Tyr Arg Ser Thr Leu Thr Ala Asn Val Val
225                 230                 235                 240

Ala Asn Val Ile Arg Asn Val Trp Ser Asn Ala Val Ile Phe Cys Gly
                245                 250                 255

His Phe Pro Asp Gly Ala Glu Lys Phe Thr Lys Thr Asp Met Ile Gly
            260                 265                 270
```

-continued

```
Glu Pro Lys Gly Gln Trp Tyr Leu Arg Gln Met Leu Gly Ser Ala Asn
275                 280                 285

Phe Asn Ala Gly Pro Ala Leu Arg Phe Met Ser Gly Asn Leu Cys His
290                 295                 300

Gln Ile Glu His His Leu Tyr Pro Asp Leu Pro Ser Asn Arg Leu His
305                 310                 315                 320

Glu Ile Ser Val Arg Val Arg Glu Val Cys Asp Arg Tyr Asp Leu Pro
325                 330                 335

Tyr Thr Thr Gly Ser Phe Leu Val Gln Tyr Gly Lys Thr Trp Arg Thr
340                 345                 350

Leu Ala Lys Leu Ser Leu Pro Asp Lys Tyr Leu Arg Asp Asn Ala Asp
355                 360                 365

Asp Ala Pro Glu Thr Arg Ser Glu Arg Met Phe Ala Gly Leu Gly Pro
370                 375                 380

Gly Phe Ala Gly Ala Asp Pro Val Thr Gly Arg Arg Arg Gly Leu Lys
385                 390                 395                 400

Thr Ala Ile Ala Ala Val Arg Gly Arg Arg Arg Ser Lys Arg Met Ala
405                 410                 415

Lys Ser Val Thr Glu Pro Asp Asp Leu Ala Ala Lys Leu His His His
420                 425                 430

His His His
435
```

MYCOBACTERIUM TUBERCULOSIS PROTEIN COMPOSITION

CROSS-REFERENCE TO RELATED APPLICATIONS

This invention claims priority to U.S. Provisional Patent Application Ser. No. 60/841,822 filed on Sep. 1, 2006, which is incorporated herein by reference.

GOVERNMENT INTERESTS

This invention was made with United States government support from the National Institutes of Health (NIH), grant number GM050853. The United States government has certain rights in this invention.

FIELD OF THE INVENTION

This invention is related to the biomedical arts. The present invention provides proteins and protein compositions that form a multiprotein desaturase complex, which allows for the characterization of enzymes involved in the synthesis of unsaturated fatty acids.

BACKGROUND OF THE INVENTION

The integral membrane desaturases are an enzyme family of immense biomedical and industrial importance. The significance of the desaturases arises from their fundamental contributions to lipid compositions and cellular homeostasis. In both eukaryotes and prokaryotes, desaturases produce essential mono- and polyunsaturated precursors to the lipid components of all cell membranes and thus help to control and maintain membrane function. Therefore, desaturases may be involved in human diseases associated with changes in lipid composition, including obesity, diabetes, hypertension, cardiovascular disease, immune disorders, degenerative neurological diseases, and skin diseases. Links between monounsaturated fatty acids and the regulation of apoptosis, neuronal differentiation, and signal transduction have been reported. The influence of monounsaturated fatty acids on apoptosis may be coupled to the development of some tumors (Lu et al., 1997, *J. Mol. Carcinog.* 20: 204-215; Falvella et al., 2002, *Carcinog.* 11: 1922-1936). Also, the fatty acid composition of erythrocyte membranes is associated with breast cancer risk (Pala et al., 2001, *J. Nat Canc. Inst.* 93: 1088-1095).

Stearoyl-CoA desaturase (SCD) catalyzes the rate-determining step in the synthesis of monounsaturated fatty acids. SCD introduces a double bond between positions 9 and 10 of stearoyl-CoA (18:0) and palmitoyl-CoA (16:0). The activity of SCD influences the fatty acid composition of membrane phospholipids, triglycerides, and cholesterol esters. Alterations of SCD activity result in changes of membrane fluidity, lipid metabolism, and metabolic rate.

Transgenic mice (*Mus musculus*) with a mutation in stearoyl-CoA desaturase 1 (SCD1) have increased energy expenditure, reduced body adiposity, and remain lean when subject to a high calorie diet, despite a higher food intake as compared to control mice (Ntambi et al., 2003, *Prog. Lipid. Res.* 43: 91-104). These findings, limited to analysis of the SCD function, link SCD function to a major health epidemic, obesity, and identify SCD as potential target for anti-obesity drugs.

Unsaturated fatty acids are also precursors of mycolic acid, a wax-like coating that protects human pathogens such as *Mycobacterium tuberculosis* from desiccation, macrophage attack, water-soluble antibiotics, and other ameliorative agents. Desaturases are of great importance to insects in the biosynthetic pathways for production of juvenile maturation hormones, and in the use of fatty acids as an energy source during swarming. Desaturases also contribute to the composition of all plant seed oils consumed by humans, and are recognized as relevant enzymes for renewable sources of hydrocarbons.

Each of the above areas involving desaturases has high impact on human health or areas of economic interest. It is therefore important to improve our understanding of the mechanisms in which fatty acid desaturation proteins function, and to understand the consequence of these enzymatic reactions on cellular structure and function.

The desaturase enzyme family is defined by the Pfam database (Bateman et al., 2004, *Nucl. Acids Res.* 32: D138-D141). SCD from yeast, rat, and mice are each members of the class III diiron family of enzymes. The hallmark of the membrane-bound SCD enzymes is that all contain an eight histidine motif (HX$_{3-4}$)H~ ~HX$_{(2-3)}$HH~ ~HX$_{(2-3)}$HH). Site-directed mutagenesis in rat SCD has demonstrated that all eight histidines are essential for activity and it was postulated that at least some of these residues were necessary for binding the iron atoms. Four isoforms of SCD have been identified in mice (SCD1-4). SCD1 is expressed largely in the liver and adipose tissue. SCD2 is expressed in the mouse brain, heart, lungs, kidney, spleen, and adipose tissue. SCD3 is expressed in the skin, Harderian gland, and preputial gland. SCD4 is expressed exclusively in the heart. These mouse isoforms are highly homologous and contain the histidine motif. The physiological roles of these different enzyme isoforms are currently not understood.

*Saccharomyces cerevisiae* (yeast) contains a single, essential gene (OLE1) that codes for a desaturase enzyme that is homologous to mouse SCDs. A yeast mutant lacking the OLE1 gene is incapable of growing in the absence of unsaturated fatty acids (UFAs). Transformation with an exogenous gene containing desaturase activity would complement an OLE1 deficient mutant.

*Mycobacterium tuberculosis* contains a single essential gene (DesA3) that codes for a desaturase enzyme that is also homologous to mouse SCDs. Disruption of the DesA3 gene in *Mycobacterium* is lethal.

DesA3 has been identified as a possible drug target for the treatment of tuberculosis. The development of efficient drugs that can inhibit or destroy the activity of this enzyme can only be accomplished upon understanding of its function. Currently, little is known about DesA3 structure and function. The characterization of DesA3 has been impaired by the lack of understanding of the composition of the enzyme system required for activity. The state of the art involves study of DesA3 alone using impure vesicle preparations obtained from mycobacterial homogenates.

It would be advantageous to identify other essential factors for the function of DesA3 and to then develop a system that will enable the determination of enhanced levels of DesA3 enzymatic activity in vitro. This knowledge could lead to a better understanding of the physiological role of DesA3 and its isoforms in vivo. The generation of such model expression system could also be used for identification of the roles of the

SUMMARY OF THE INVENTION

The present invention provides isolated proteins that include an amino acid sequence represented by SEQ ID NO: 9. The isolated proteins are capable of influencing the desaturation of fatty acids. The isolated proteins may have at least 90% sequence identity to SEQ ID NO: 9, or they may have at least 95% sequence identity to SEQ ID NO: 9. The isolated proteins may include at least 380 amino acids of SEQ ID NO: 9.

The invention further provides an isolated protein composition from *Mycobacterium tuberculosis*, which includes a desaturase and an oxidoreductase. The protein composition is capable of influencing desaturation of fatty acids. The desaturase can have at least 95% amino acid sequence identity to Rv3229c, and the oxidoreductase can have at least 95% amino acid sequence identity to Rv3230c. Alternatively, the desaturase can be Rv3229c, and the oxidoreductase can be Rv3230c. In some embodiments, the isolated protein composition may include both Rv3229c and Rv3230c.

The desaturase can be selected from the group consisting of a fatty acid desaturase capable of inserting double bonds into fatty acyl chains derivatized to CoA, glycerols, alkyl ethers, alkenyl ethers, phosphatides, mycolic acids, or glycosidic sugars. Preferably, the desaturase is *Mycobacterium tuberculosis* DesA3 (also known as Rv3229c).

The oxidoreductase can be selected from the group consisting of oxidoreductases that are specific for NADH or NADPH, and that reduce enzyme-bound metal ions including heme groups, iron-sulfur centers and those bound by amino acid side chains such as histidine, glutamate, aspartate, cysteine, or tyrosine. The oxidoreductase can be cytochrome b5. The oxidoreductase can be cytochrome b5 reductase. The oxidoreductase can be a flavoprotein. The oxidoreductase can be an iron-sulfur protein. The oxidoreductase may contain properties of both flavoprotein and iron-sulfur proteins. The oxidoreductase may originate in Gram-positive actinomycetes such as *Mycobacterium tuberculosis, Mycobacterium leprae, Mycobacterium bovis, Mycobacterium avis, Mycobacterium smegmatis*, and others. Preferably, the oxidoreductase is *Mycobacterium tuberculosis* Rv3230c.

The present invention also relates to methods of screening target ligands specific for a desaturase complex. The methods include preparing a first mixture containing a desaturase and an oxidoreductase by expressing one or more first genes encoding the desaturase and expressing one or more second genes encoding the oxidoreductase, contacting the first mixture with a fatty acid to form a second mixture, contacting the second mixture with a target ligand, and determining the activity of the desaturase. The change in activity of the desaturase is correlated with binding of the target ligand to the desaturase complex.

DETAILED DESCRIPTION OF THE INVENTION

General Overview

Figure 1:
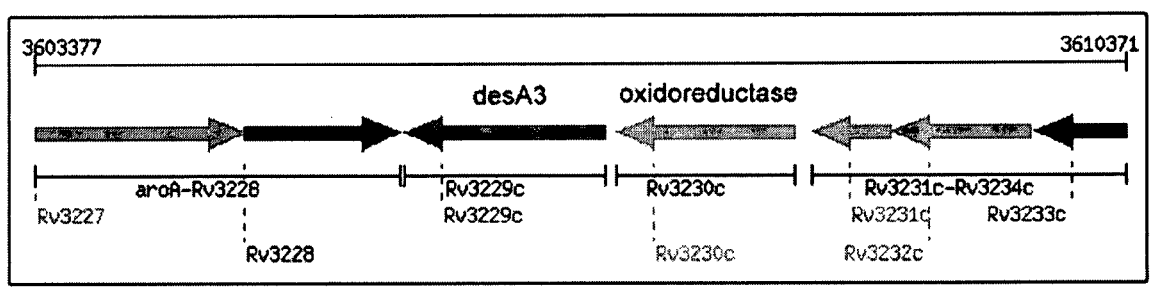
FIG. 1 is a schematic diagram of the *Mycobacterium tuberculosis* multi-protein desaturase complex.

The practice of the present invention employs, unless otherwise indicated, conventional techniques of molecular biology (including recombinant techniques), microbiology, cell biology, biochemistry, immunology, protein kinetics, and mass spectroscopy, which are within the skill of art. Such techniques are explained fully in the literature, such as in Sambrook et al., 2000, *Molecular Cloning: A Laboratory Manual*, third edition, Cold Spring Harbor Laboratory Press, Cold Spring Harbor; N.Y.; Sambrook et al., 1989, *Molecular Cloning: A Laboratory Manual*, second edition, Cold Spring Harbor Laboratory Press, Cold Spring Harbor, N.Y.; Ausubel et al., 1987-2004, *Current Protocols in Molecular Biology*, Volumes 1-4, John Wiley & Sons, Inc., New York, N.Y.; Kriegler, 1990, *Gene Transfer and Expression: A Laboratory Manual*, Stockton Press, New York, N.Y.;. Dieffenbach et al., 1995, *PCR Primer: A Laboratory Manual*, Cold Spring Harbor Laboratory Press, Cold Spring Harbor, N.Y., each of which is incorporated herein by reference in its entirety. Procedures employing commercially available assay kits and reagents typically are used according to manufacturer-defined protocols unless otherwise noted.

Generally, the nomenclature and the laboratory procedures in recombinant DNA technology described below are those well known and commonly employed in the art. Standard techniques are used for cloning, DNA, RNA, and protein isolation, nucleic acid amplification, and nucleic acid and protein purification. Generally enzymatic reactions involving DNA ligase, DNA polymerase, restriction endonucleases and the like are performed according to the manufacturer's specifications.

DEFINITIONS

"Desaturases" refer to enzymes that remove two hydrogen atoms from adjacent carbons in an organic compound, creating a carbon/carbon double bond. Such enzymes can be found in humans and other eukaryotes (such as monkeys, rats, mice, zebrafish, cows, pigs, sheep, chickens, yeast, and others), in beneficial microorganisms (such as *Streptomyces colieocolor, Streptomyces avermitilis* and other bacteria that are responsible for the synthesis of a wide array of antibiotics), and in pathogens (such as *Mycobacterium tuberculosis, Mycobacterium leprae, Mycobacterium bovis, Mycobacterium avis*, and many other Gram-positive actinomycetes).

"Nucleic acid" or "polynucleotide sequence" refers to a single or double-stranded polymer of deoxyribonucleotide or ribonucleotide bases read from the 5' to the 3' end. Nucleic acids may also include modified nucleotides that permit correct read-through by a polymerase and do not alter expression of a polypeptide encoded by that nucleic acid.

"Nucleic acid sequence encoding" refers to a nucleic acid that directs the expression of a specific protein or peptide. The nucleic acid sequences include both the DNA strand sequence that is transcribed into RNA, and the RNA sequence that is translated into protein. The nucleic acid sequences include both the full length nucleic acid sequences as well as non-full length sequences derived from the full length sequences. It should be further understood that the sequence includes the degenerate codons of the native sequence or sequences that may be introduced to provide codon preference in a specific host cell.

"Coding sequence" or "coding region" refers to a nucleic acid molecule having sequence information necessary to produce a gene product, when the sequence is expressed.

"Nucleic acid construct" or "DNA construct" refers to a coding sequence or sequences operably linked to appropriate regulatory sequences so as to enable expression of the coding sequence.

"Isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated nucleic acid of the present invention is separated from open reading frames that flank the desired gene and encode proteins other than the desired protein. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 25% sequence identity. Alternatively, percent identity can be any integer from 25% to 100%. More preferred embodiments include at least: 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98% or 99% compared to a reference sequence using the programs described herein; preferably BLAST using standard parameters, as described. One of skill will recognize that these values can be appropriately adjusted to determine corresponding identity of proteins encoded by two nucleotide sequences by taking into account codon degeneracy, amino acid similarity, reading frame positioning and the like.

"Substantial identity" of amino acid sequences for purposes of this invention normally means polypeptide sequence identity of at least 40%. Preferred percent identity of polypeptides can be any integer from 40% to 100%. More preferred embodiments include at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 98.7%, or 99%. Polypeptides that are "substantially identical" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

A protein "isoform" is a version of a protein with some small differences. For example, the small differences may be a result of a splice variant of the protein, or they may be the result of some post-translational modification. Often, an isoform of an enzyme may have different catalytic properties than the native form of the enzyme.

A "protein composition", as used herein, refers to a composition comprising two or more proteins mixed together.

A "desaturase system" or "desaturase complex" refers to two or more components that are mixed together in order to facilitate the desaturation of fatty acids. Such components may include enzymes, e.g. desaturase, cytochrome b5, cytochrome b5 reductase, and others. The components may further include other proteinaceous or non-proteinaceous molecules that are involved in desaturation of fatty acids. These components may interface together. The components of the desaturase system may be structurally or functionally related.

A "target ligand" refers to a ligand that can be identified and/or isolated through a specific binding to one or more components of the desaturase system. For example, the target ligand may be a protein, an enzyme, an antibody, an enzymatic substrate, or a drug. Binding of the target ligand to one or more components of the desaturase system is dependent upon the specificity of the binding site(s) of the one or more components of the desaturase system to the target ligand. Binding of the target ligand may influence the activity of the desaturase. The change in activity can be measured, e.g., using a desaturation assay.

An "enzyme assay" or "enzymatic assay" refers to a standard laboratory method for measuring enzymatic activity. An enzymatic assay for determination of desaturase activity ("desaturation assay") refers to a laboratory method for determining the activity of the enzyme involved in fatty acid desaturation (desaturase).

In one example, the change in 18:1-CoA production can be used for determination of the desaturase activity. A method for assay of 18:1-CoA production is provided as follows. Radioactive fatty acyl-CoAs were obtained from American Radiolabeled Chemicals (St. Louis, Mo.). The reaction mixture contained 20 mM of potassium phosphate and 150–250 mM of NaCl in a total reaction volume of 200 µL. Aliquots (20 µL) of the *M. smegmatis* pVV16 control lysate or pVV16-DesA3 total lysate, supernatant or pellet fractions were added in various combinations with aliquots (15 µL) of supernatant fraction prepared from either *E. coli* pQE80 control supernatant or pQE80-Rv3230c. The reaction was initiated by addition of 0.4 µmol of NADPH, 6 nmol of stearoyl-CoA, 0.03 µCi of [1-$^{14}$C]-stearoyl-CoA and 0.2 nmol of FAD in a combined volume of 200 µL. The reaction was incubated at 37° C. for 1 h and stopped by the addition of 200 µL of 2.5 M KOH in ethanol. The mixture was heated at 80° C. for 1 h and acidified by the addition of 280 µL of formic acid. The saponified fatty acids were extracted with 700 µL of hexane, 200 µL of the extract was evaporated to dryness, resuspended in 50 µL of hexane and separated into saturated and unsaturated acids on a 10% AgNO$_3$-impregnated thin-layer chromatography plate using chloroform:methanol:acetic acid:water (90:8:1:0.8) as the developing solvent. Radioactivity was counted by phosphorimaging using a Packard Instant Imager (Packard, Meriden, Conn.) for 30-60 min. Samples prepared in this manner gave ~200 total imager units for the major radioactive bands detected, which is within the linear response range of the instrument. Reactions performed with stearoyl-CoA were also treated by thin-layer chromatography as described above, and the individual bands were extracted from the plate, methylated and analyzed by GC/MS to determine fatty acid content.

Desaturases

The present invention provides methods for expression of various desaturases as part of the desaturase expression system. The desaturases may be eukaryotic (e.g. of human, animal, or plant origin) and prokaryotic (e.g. of bacterial origin). For example, desaturases useful for practicing of the invention include soluble desaturases and membrane-bound desaturases, acyl-lipid desaturases, acyl-coenzyme A (acyl-CoA) desaturases, acyl-acyl carrier protein (ACP) desaturases, and other desaturases. Desaturases can be substrate-specific, which means that they can preferably catalyze the oxidation-reduction reactions of specific substrates. For example, an oxidoreductase that is specific for a CH—CH group of donors preferably catalyzes oxidation-reduction reactions of substrates containing CH—CH groups to produce alkene bonds. Preferably, the desaturase is a stearoyl-CoA desaturase.

Oxidoreductases

The present invention provides methods for expression of various oxidoreductases as part of the desaturase expression system. Oxidoreductases are enzymes of EC class 1. Oxidoreductases catalyze oxidation-reduction reactions, which entail the transfer of electrons from a substrate that becomes oxidized (electron donor) to a substrate that becomes reduced (electron acceptor).

The oxidoreductases can be substrate-specific, which means that they can preferably catalyze the oxidation-reduction reactions of specific substrates. For example, an oxidoreductase that is specific for a CH—CH group of donors preferably catalyzes oxidation-reduction reactions of substrates containing CH—CH groups. Another form of oxidoreductase may be specific for transfer of electrons to a protein substrate such as another oxidoreductase. Preferably, the oxidoreductases for practicing the invention are cytochrome b5, cytochrome b5-like proteins, and cytochrome b5 reductase, *Mycobacterium tuberculosis* H37Rv oxidoreductase Rv3230c and related proteins from other prokaryotes.

Vectors

The invention involves genetically engineering a system for the expression of enzymes involved in fatty acid desaturation. The genetic engineering may include increasing the amount of enzymes involved in desaturation. However, in other instances, the genetic engineering may additionally include expression of other non-enzymatic components that are involved in desaturation.

Engineering of the desaturase expression system involves providing for the expression of one or more heterologous genes that encode protein(s) involved in desaturation. The heterologous gene may be a gene that is not naturally present in the desaturase system, or it may be a gene that is naturally present but is placed in a different genetic context (e.g., the coding region of the gene is operably linked to a promoter that is not the gene's natural promoter). Typically, the heterologous gene or the resulting protein will have one or more properties differing from the gene in its natural genetic environment.

One method of expression of proteins of the desaturase system of this invention is through the use of vectors such as plasmids, phage, phagemids, viruses, artificial chromosomes and the like. Preferred vectors are expression vectors. Expression vectors contain a promoter that may be operably linked to a coding region. A gene or coding region is operably linked to a promoter when transcription of the gene initiates from the promoter. More than one gene may be operably linked to a single promoter. In preferred embodiments, at least one desaturase gene and at least one oxidoreductase gene are both operably linked to the same promoter. In other preferred embodiments, at least one desaturase gene, at least one cytochrome b5 gene, and at least one cytochrome b5 reductase gene are operably linked to the same promoter. In other preferred embodiments, each of the genes is operably linked to a different promoter. In one aspect, the vector is introduced into an organism that is suitable for expression of the desaturase system.

A variety of expression vectors may be used for expression in *E. coli*, insect, yeast, or mammalian cells. Expression vectors that may be used include, but are not limited to, Gateway® Destination vectors (Invitrogen, Carlsbad, Calif.), pQE-30, pQE-40, and pQE-80 series (Qiagen, Valencia, Calif.), pUC19 (Yanisch-Perron et al., 1985, *Gene* 33: 103-119), pBluescript II SK+ (Stratagene, La Jolla, Calif.), the pET system (Novagen, Madison, Wis.), pLDR20 (ATCC 87205), pBTrp2, pBTac1, pBTac2 (Boehringer Ingelheim Co., Ingelheim, Germany), pLSA1 (Miyaji et al., 1989, *Agric. Biol. Chem.* 53: 277-279), pGEL1 (Sekine et al., 1985, *Proc. Natl. Acad. Sci. USA.* 82: 4306-4310), and pSTV28 (manufactured by Takara Shuzo Co., Shimogyo-ku, Kyoto 600-8688, Japan). When a yeast strain is used as the host, examples of expression vectors that may be used include pYEST-DES52 (Invitrogen), YEp13 (ATCC 37115), YEp24 (ATCC 37051), and YCp50 (ATCC 37419). When insect cells are used as the expression host, examples of expression vectors that may be used include Pfastbac1 (Invitrogen, Carlsbad, Calif.), pVL1393 (BD Biosciences, Franklin Lakes, N.J.) and pIEX (Novagen, Madison, Wis.).

Alternatively, expression kits might be utilized for cell-free protein expression. For example, the EasyXpress Protein Synthesis Mini Kit, the EasyXpress Protein Synthesis Mega Kit (Qiagen), the In vitro Director™ System (Sigma-Aldrich, St. Louis, Mo.), the TnT Sp6 High-Yield Protein Expression System (Promega; Madison, Wis.) or the WePro lysate (Cell Free Sciences, Yokohama, Japan) might be used. Examples of expression vectors used for cell-free protein expression include pIX4 (Qiagen; Valencia, Caif.), pFK (Promega, Madison, Wis.) and pEU (Cell Free Sciences, Yokohama, Japan).

Expression of the components of the desaturase system is controlled with the use of desirable promoters. Essentially any promoter may be used as long as it can be expressed in the engineered organism. A preferred promoter for *E. coli* is the lambda $P_R$ promoter. In the presence of the product of the lambda $C_I$ repressor gene, transcription from the lambda $P_R$ promoter may be controlled. At temperatures below 37° C., the repressor is bound to the lambda $P_R$ promoter and transcription does not occur. At temperatures above 37° C. the repressor is released from the lambda $P_R$ promoter and transcription initiates. Thus, by growing the organism containing the vector at 37° C. or above, the genes are expressed.

In one example, a preferred promoter for *E. coli* is the lac promoter. In the presence of allolactose, an alternative product of the metabolism of lactose by beta-galactosidase, transcription from the lac promoter may be controlled. In the absence of allolactose, the lac repressor is bound to the lac operator and transcription does not occur. In the presence of allolactose, the repressor is released from the lac operator and transcription initiates. Thus, by growing the organism containing the vector containing lac operator sequences and lac repressor in the presence of allolactose, the genes are expressed.

When the organism is a yeast cell, any promoter expressed in the yeast strain host can be used. Examples include the gal 1 promoter (GAL1), leucine2 promoter (LEU2), tryptophan promoter (TRP), gal 10 promoter, heat shock protein promoter, MF alpha 1 promoter, and CUP 1 promoter.

A ribosome-binding sequence (RBS) (prokaryotes) or an internal ribosome entry site (IRES) (eukaryotes) may be operably linked to the gene. The RBS or IRES is operably linked to the gene when it directs proper translation of the protein encoded by the gene. It is preferred that the RBS or IRES is positioned for optimal translation of the linked coding region (for example, 6 to 18 bases from the initiation codon). In vectors containing more than one gene, it is preferred that each coding region is operably linked to an RBS or IRES. A preferred RBS is AGMGGAG.

The gene or genes encoding components of the desaturase complex may also be operably linked to a transcription terminator sequence. A preferred terminator sequence is the T7 terminator (pET15b; Novagen, Madison, Wis.).

The coding region of the gene may be altered prior to insertion into or within the expression vector. These mutants may include deletions, additions, and/or substitutions. When alterations are made, it is preferred that the alteration maintains the desired enzymatic function or specificity of the enzyme. However, in certain embodiments, it may be desired to alter the specificity of the enzyme. For example, one may wish to alter an oxidoreductase such that the activity of the enzyme is changed. As another example, altering an oxidoreductase may change physical properties such as stability or solubility.

When a heterologous gene is to be introduced into an organism that does not naturally encode the gene, optimal expression of the gene may require alteration of the codons to better match the codon usage of the host organism. The codon usage of different organisms is well known in the art.

The coding region also may be altered to ease the purification or immobilization. An example of such an alteration is the addition of a "tag" to the protein. Examples of suitable tags include FLAG, polyhistidine, biotin, T7, S-protein, myc-, and GST (Novagen; pET system). In a preferred embodiment, the gene is altered to contain a hexo-histidine tag in the N-terminus. The protein may be purified by passing the protein-containing solution through a $Ni^{2+}$ column.

In other embodiments, the coding regions of two or more enzymes are linked to create a fusion protein. In preferred embodiments, a desaturase-cytochrome b5 fusion protein is encoded. In another preferred embodiment, the fusion protein comprises a desaturase-cytochrome b5 reductase.

In further preferred embodiments, the expression vector of the present invention comprises at least one polynucleotide sequence encoding a desaturase and at least one polynucleotide sequence encoding an oxidoreductase. The plasmid may also encode one or more enzymes that facilitate fatty acid desaturation.

Expression of a Desaturase System

The optimal function of a multi-protein enzyme complex such as desaturase requires the presence of all members of the enzyme complex. In one aspect, the invention provides a recombinant expression system that includes components of a desaturation complex that are involved in fatty acid desaturation. Preferably, these components are enzymes. At minimum, the desaturation complex includes two enzymes: desaturase and oxidoreductase. In various aspects of the invention, different forms of desaturases and oxidoreductases may be used. For example, they may be native (full-length), truncated, mutated, or otherwise modified by methods known in the art. With respect to the expression system, the desaturase and oxidoreductase may be homologous, heterologous, or may constitute mixtures thereof (i.e., one or more enzymes are homologous, whereas other one or more enzyme are heterologous).

In one aspect, the present invention provides a multi-protein desaturase complex from *Mycobacterium tuberculosis*. The complex includes Rv3229c and Rv3230c gene products. The amino acid sequence of the Rv3230c gene product is shown in SEQ ID NO: 9. The complex may also include additional gene products.

In one embodiment, individual plasmids may express individual gene products that form the desaturase complex. For example, if several plasmids are used for expression, each plasmid may carry one or more genes encoding one or more components of a mycobacterial desaturase complex. Alternatively, a vector may carry more than one gene encoding more than one component of a mycobacterial desaturase complex. Thus, expression of multiple proteins of a mycobacterial desaturase complex may be achieved with the use of only one vector.

In a different aspect, the invention provides multiple vectors that express components of a desaturase complex. In one embodiment, individual plasmids may express individual gene products that form the desaturase complex. For example, if several plasmids are used for expression, each plasmid may carry one gene encoding one or more components of a desaturase complex. Alternatively, one vector may carry more than one gene, each gene encoding one or more components of a desaturase complex. Thus, expression of multiple proteins of a desaturase complex may be achieved with the use of only one vector.

In a preferred embodiment, the genes encoding components of a desaturase complex are present in equal proportions. This can be accomplished in a variety of ways, for example by using one vector that has equal proportions of genes from a desaturase complex. These genes may be inserted under the control of same control elements for gene expression. One vector may carry sequences encoding more than one component of the complex. In one embodiment, the vector might carry three components of the desaturase complex, present in a certain ratio. In a preferred embodiment, the ratio of Rv3230c and Rv3229c coding sequences is 1:1 or the ratio of SCD, cytochrome b5 and cytochrome b5 reductase coding sequences is 1:1:1. Alternatively, individual genes of the desaturase complex may be expressed using separate plasmids. In that case, each plasmid of the expression system may carry at least one gene encoding a component of the complex, while all plasmids have identical control elements for gene expression.

In a different embodiment, the invention provides a cell-free expression system for desaturases, where genes that encode the desaturase complex are added to the system, proteins are expressed, and enzymatic activities are determined. The proteins that form the desaturase complex may be introduced by any method known in the art. Preferably, proteins that form the desaturase complex include Rv3229c (mycobacterial DesA3) and Rv3230c (mycobacterial DesA3 oxidoreductase) or SCD, cytochrome b5, and cytochrome b5 reductase. Cell-free expression of one or more components of the desaturase system obviates the need for assembly of multiple genes in an expression vector to achieve co-expression. Instead, transcribed mRNA from plasmid can be added to achieve any ratio of translated protein. That is why in some examples it may not be necessary to put multiple genes into expression plasmid backbones.

The desaturase may exist as a separate enzyme or may be a genetic fusion with an oxidoreductase domain.

The invention also provides an assay system for determination of desaturase activity. Preferably, the system includes at least one expression vector, preferably a vector that includes genes encoding a desaturase and an oxidoreductase. In a preferred embodiment, the vector includes sequences encoding Rv3230c and Rv229c, with the ratio of coding sequences being 1:1. Desaturase activity assays may be conducted with variants of the components of the expression system. For example, different expression vectors may be used. Also, the individual components that are expressed may be varied. For example, in another preferred embodiment, Rv3229c (mycobacterial DesA3) and Rv3230c (mycobacterial DesA3 oxidoreductase) are combined in a ratio of 10:1. As another example, a homolog or a mutant protein may be expressed as a part of the desaturase complex, to study its role in the enzymatic reactions.

In some embodiments, different variants of the genes or proteins are introduced. These include homologs, mutants, proteins with amino acids substitutions, etc., depending on the objective of the investigation.

It is further possible to optimize the cell-free expression system of this invention by stabilizing each of the components of the desaturase system in its own stabilizing buffer, using methods known in the art.

In a further aspect the present invention includes a desaturase complex together with at least one co-factor, isolated in its pure form, and then added to the desaturase complex.

The present invention further provides screening methods that can be used to identify target ligands that bind to a desaturase complex that is involved in desaturation of fatty acids. The target ligands can be for example be proteins or drugs.

In some aspects, the target ligands can be labeled. The method of screening target ligands specific for a desaturase complex includes expressing one or more genes encoding a desaturase, expressing one or more genes encoding an oxidoreductase, contacting the expressed desaturase and oxidoreductase with a fatty acid, providing a target ligand, incubating the target ligand with the expressed desaturase and with the expressed oxidoreductase, and determining the increase in activity of 18:1-CoA production, thereby determining whether or not the target ligand binds to the desaturase complex. For example, if the target ligand is a drug molecule, the target ligand may influence the activity of the desaturation complex, thereby changing (increasing or decreasing) fatty acid desaturation, as measured by 18:1-CoA production. One skilled in the art can thus evaluate the efficiency of various target ligands (e.g. drug molecules) for desaturation of fatty acids.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

It is to be understood that this invention is not limited to the particular methodology, protocols, patients, or reagents described, and as such may vary. It is also to be understood that the terminology used herein is for the purpose of describing particular embodiments only, and is not intended to limit the scope of the present invention, which is limited only by the claims. The following examples are offered to illustrate, but not to limit the claimed invention.

Materials

Total genomic DNA of *Mycobacterium tuberculosis* H37Rv was obtained from the TB Research Materials Facility at Colorado State University (Prof. J. Belisle, Director, NIH NIAD NO1AI75320). This material was used to clone rv3230c and rv3229c (encoding DesA3) by PCR methods.

Total RNA is obtained from mouse liver (SCD1), brain (SCD2), Harderian gland (SCD3), and heart (SCD4) using the TRIzol reagent (Invitrogen). AMV Reverse Transcriptase is from Promega (Madison, Wis.), and AccuPrime™ Pfx DNA polymerase is from Invitrogen (Carlsbad, Calif.).

Gene Cloning

The rv3230c gene was amplified by PCR using the primers 5'-cgggGT-ACCatcgagggaaggatgagcaagaaacacacgac-3' (SEQ ID NO: 1) and 5'-cccMG-CTTctagatgtccagcacgcaat-cac-3' (SEQ ID NO: 2). The KpnI and HindIII restriction sites are indicated in capital letters. The PCR contained 10% dimethyl sulfoxide and consisted of 30 cycles of melt, anneal and extend at temperatures of 94° C., 55° C. and 72° C., respectively. The resulting DNA fragment was purified by gel electrophoresis and extracted using a QIAquik Gel Extraction Kit (Qiagen). The PCR product was digested with KpnI and HindIII and ligated into similarly digested pQE80 vector to create expression vector pQE80-Rv3230c. *E. coli* TOP10 pQE80-Rv3230c transformants were cultured on either Luria-Bertani broth or agar medium, both containing 100 µg/mL of ampicillin. Plasmids isolated from these cells were used to verify the sequence of the PCR-cloned gene.

The rv3229c gene (encoding DesA3) was amplified using the primers 5'-gggaattcCATATGgcgatcact-gacgtcgacgtattcgcg-3' (SEQ ID NO: 3) and 5'-ccc-AAGCT-Tggctgccagatcgtcgggttcgg-3' (SEQ ID NO: 4). The NdeI and HindIII restriction sites are indicated in capital letters. The PCR contained 10% dimethyl sulfoxide and consisted of 30 cycles of melt, anneal, and extend at temperatures of 94° C., 55° C., and 72° C., respectively. The resulting DNA fragments were purified by gel electrophoresis and extracted using a QIAquik Gel Extraction Kit. The PCR product was digested with NdeI and HindIII and ligated into the similarly digested pVV16 to create expression vector pVV16-DesA3. *E. coli* TOP10 pVV16-DesA3 transformants were cultured on either Luria-Bertani broth or agar medium containing 50 µg/mL of kanamycin. Plasmids isolated from these cells were used to verify the sequence of the PCR-cloned gene.

Table 1 shows custom designed primers used to clone SCD genes by a three-step PCR approach. The custom designed primers (Table 1) utilized in the three reactions are synthesized by and purchased from Integrated DNA Technologies (Coralville, Iowa). The gene-specific primer (SEQ ID NO: 5) is used in the first PCR reaction to isolate the SCD gene and incorporate a portion of the OLE1 starter sequence. The $2^{nd}$ Forward primer (SEQ ID NO: 6) is used in the second PCR reaction to incorporate the remainder of the OLE1 starter sequence. The $3^{rd}$ Forward primer (SEQ ID NO: 7) is used in the third PCR reaction to incorporate a ribosomal binding site and the recombination site for Gateway® cloning at the 5' end of the gene. The Reverse primer (SEQ ID NO: 8) is used in all three PCR reactions to incorporate a recombination site for Gateway® cloning at the 3' end of the gene. The stop codon is eliminated from the open reading frame using the Reverse primer such that the 6× His tag from the pYES-DEST52 plasmid would be incorporated.

Total RNA is obtained from mouse liver (SCD1), brain (SCD2), Harderian gland (SCD3), and heart (SCD4) using the TRIzol reagent. AMV Reverse Transcriptase is used to generate cDNA from the total RNA. Each plasmid is then used as the template in a three-step PCR. The first and second PCRs incorporated a 27-amino acid sequence representative of the 27 N-terminal codons of the OLE1 gene, which code for the endoplasmic reticulum (ER) localization sequence. Then, a ribosomal binding site and the recombination sites required for Gateway® cloning are introduced. By way of the pDONR221 entry clone, Invitrogen's Gateway® cloning technology incorporated each gene into the yeast expression plasmid pYES-DEST52. Sequencing of the entire gene is performed to ensure no mutations are introduced during the PCR reactions. The GAL1 promoter induces the expression of the gene in the presence of galactose and the 6× His tag allows for Western blot detection using a His-tag Monoclonal antibody kit available from Novagen.

To create a more stable variant of the SCD protein, one that is not easily degraded by an ER protease at the N-terminal, a truncated form of each mouse SCD isoform is created. PCR primers are designed to eliminate approximately 30 of the first amino acids corresponding to the protease site.

Time course expression trials are completed by first inoculating a 10 ml culture (synthetic culture medium without uracil {SC-U} containing 2% glucose and 0.5 mM UFAs) with a single isolated colony. The culture is grown overnight at 30° C. with agitation set at 280 rpm. After ~30 hr of incubation the amount necessary to yield an $OD_{600}$ of 0.4 in a 50 ml culture is transferred to a clean culture tube. The cells are harvested by centrifugation at 3000×g for 10 minutes, resuspended in a small volume of SC-U medium containing 2% galactose (-UFAs), and this solution is used to inoculate a 50 mL of SC-U medium with 2% galactose. Cells are grown at 30° C. with agitation set at 280 rpm and samples are taken at 0, 4, 8, 12, 16, and 24 hours.

Expression of Rv3230c. *E. coli* Rosetta2 (Novagen, Madison Wis.) transformed with pQE80-Rv3230c was used for expression studies. The transformed strain was cultured on either Terrific Broth or Luria-Bertani agar medium containing 34 μg/mL of chloramphenicol and 100 μg/mL of ampicillin. Expression of Rv3230c was induced by addition of IPTG to 0.5 mM and continued overnight at 16° C. The cells harvested from a 2-L culture (~5 g) were washed once in 20 mM $NaH_2PO_4$, pH 7.2, containing 150 mM NaCl and re-suspended in the same buffer at a composition of 1 g of wet cell paste per 2 mL of buffer. The amino acid sequence of Rv3230c is shown in SEQ ID NO: 9.

Fractionation of Rv3230c. The cell suspension was sonicated for a total of 150 s using a duty cycle of 15 s on and 45 s off (Fisher Model 550 Sonic Dismembrator, ⅛-in horn).

TABLE 1

Custom designed primers utilized in the three-step PCR for SCD cloning

| Name | Sequence | SEQ ID NO | Primer Info |
|---|---|---|---|
| Gene-specific | 5'-CCA AAG GAT GAC TCT GCC AGC AGT GGC ATT GTC GAC (+ gene specific region)-3' | 5 | Forward primer containing gene specific overlap region plus portion of OLE1 starter sequence. |
| $2^{nd}$ Forward | 5'-CCA ACT TCT GGA ACT ACT ATT GAA TTG ATT GAC GAC CAA TTT CCA AAG GAT GAC TCT GCC-3' | 6 | Forward primer containing remainder of OLE1 starter sequence. |
| $3^{rd}$ Forward | 5'-GGGG ACA AGT TTG TAC AAA GCA GGC TCC AATA ATG TCT CCA ACT TCT GGA ACT ACT ATT G-3' | 7 | Forward primer containing ribosomal binding site and recombination site for Gateway ® cloning. |
| Reverse | 5'-GGGG AC CAC TTT GTA CAA GAA AGC TGG GTC (+ gene specific region [lacking stop codon])-3' | 8 | Reverse primer containing recombination site for Gateway ® cloning. |

Protein Expression

Each SCD expression plasmid is transformed into the yeast strain L8-14C, an OLE1 deficient yeast mutant, according to the *Saccharomyces cerevisiae* EasyComp Transformation Kit (Invitrogen). Transformed cells are cultured on plates containing minimal medium (0.67% yeast nitrogen base w/o amino acids; 0.2% casamino acids; 2% Bacto™ agar) plus 0.005% histidine, 0.01% leucine, 2% D-glucose, and 0.5 mM UFAs. Cells are then selected from the plates and streaked on minimal medium plates containing 0.005% histidine, 0.01% leucine, and 2% D-galactose. Galactose induces expression of the inserted gene by acting on the GALL promoter region of the pYES-DEST52 plasmid.

During sonication, the temperature of the cell suspension was maintained below 10° C. by placing the beaker in an ice water bath containing NaCl. The sonicated cell suspension was centrifuged at 27,000 g for 30 min and the supernatant fraction was retained for activity assays.

Cloning of DesA3. The rv3229c gene (encoding DesA3) was amplified using the primers 5'-gggaattcCATATGgcgat-cactgacgtcgacgtattcgcg-3' (SEQ ID NO:3) and 5'-cccAAGCTTggctgccagatcgtcgggttcgg-3' (SEQ ID NO:4'. The NdeI and HindIII restriction sites are indicated in capital letters. The PCR contained 10% dimethyl sulfoxide and consisted of 30 cycles of melt, anneal, and extend at temperatures of 94° C., 55° C., and 72° C., respectively. The resulting DNA fragments were purified by gel electrophoresis and extracted using a QIAquik Gel Extraction Kit. The PCR product was digested with NdeI and HindIII and ligated into the similarly digested pVV16 to create expression vector pVV16-DesA3. *E. coil* TOP10 pVV16-DesA3 transformants were cultured on either Luria-Bertani broth or agar medium containing 50 μg/mL of kanamycin. Plasmids isolated from these cells were used to verify the sequence of the PCR-cloned gene.

Expression of DesA3. *Mycobacterium smegmatis* (ATCC 700084) was transformed by electroporation with either pVV16-DesA3 or pVV16 containing no insert. These transformants were maintained on either Middlebrook 7H10 agar medium or Middlebrook 7H9 broth enriched with Middlebrook OADC (oleic acid-albumin-dextrose-catalase, Becton Dickinson, Spark Md.) and 20 μg/mL kanamycin. The expression studies were performed in 2-L of the enriched medium. DesA3 was constitutively expressed at 37° C. The cells were grown for ~38 h, harvested by centrifugation and washed once in 20 mM $NaH_2PO_4$, pH 7.2, containing 500 mM NaCl. The amino acid sequence of Rv3229c is shown in SEQ ID NO: 10.

Preparation of *M. smegmatis* Lysate. The cell paste was re-suspended in the wash buffer at a composition of 1 g of wet cell paste per 2 mL of buffer. The cell suspension was sonicated for a total of 480 s using a duty cycle of 15 s on and 45 s off with the temperature of the suspension maintained below 10° C. A fraction of the total lysate was retained for assays and other analyses and the remainder was centrifuged at 27,000×g for 30 min to separate the supernatant and the pellet fractions. The soluble fraction was removed and the pellet fraction was re-suspended in the same volume as total cell lysate subjected to centrifugation. The three samples were then treated with the same amount of 50 mM Tris-HCl, pH 7.4, containing 150 mM NaCl, 1 mM phenylmethysulfonyl fluoride, 1 mM EDTA, 1% Triton X-100, 1% sodium deoxycholate, and 0.1% SDS.

For immunoprecipitation, the expressed DesA3 was treated with the primary mouse anti-His-tagged antibody and analyzed by trypsin digestion and mass spectrometry as described for Rv3230c.

Cloning of all enzymes is designed such that a His (6×)-tag is incorporated to facilitate detection of the expressed protein by Western and purification by affinity chromatography. To determine the optimal time for cell harvest after induction, samples are taken at different times and the expression is assessed by Western blot.

Western Blot

The cell lysates were analyzed for total expression and the presence of Rv3230c in the soluble fraction by Western blotting with primary mouse anti-His-tagged antibody (Novagen) and SDS-PAGE. Samples were prepared and fractionated for SDS-PAGE using approaches developed for high-throughput structural genomics studies. For the immunoprecipitation, the lysate was treated with antibody and then the antigen-antibody complex was precipitated by addition of Protein G-linked Sepharose resin (Amersham, Piscataway, N.J.). The precipitated sample of Rv3230c was purified by SDS-PAGE and further analyzed by trypsin digestion and mass spectrometry at the University of Wisconsin Biotechnology Center.

In Vivo Activity Assay

Full-length and truncated versions of each mouse isoform, SCD1-SCD4 and mycobacterial DesA3, were successfully amplified and cloned. The use of Gateway® technology averaged >95% efficiency. Each SCD isoform is transformed into the OLE1 deficient yeast strain L8-14C. Transformed cells are capable of growing on minimal medium plates containing histidine, leucine, D-glucose, and UFAs, or on minimal medium plates containing histidine, and D-galactose, in the absence of unsaturated fatty acids. The results are summarized in Table 2. These experiments proved that that the enzymes are active in vivo. Note that the SCD4 enzyme appeared to differ from the other isoforms as the transformed yeast exhibited different growth patterns.

TABLE 2

Comparison of expression systems for the mammalian stearoyl-CoA desaturases (4 mouse (m) isoforms, 2 human (h) isoforms, and 1 mycobacterial (DesA3) isoform

| Enzyme | Protein constructs available | In vivo activity |
|---|---|---|
| mSCD1 | Full-length and truncate | ++++++ |
| mSCD2 | Full-length and truncate | ++++ |
| mSCD3 | Full-length and truncate | +++++ |
| mSCD4 | Full-length and truncate | Not active |
| hSCD1 | ole 1 chimera | +++ |
| hSCD5 | Wild-type | +++++ |
| DesA3 | Wild-type and ole 1 chimera | None without Rv32320c |

TABLE 3

Comparison of reconstituted complexes of recombinant mSCD1 (heterologous expression; prepared as yeast microsomes) with exogenous recombinant cyt b5 and cyt b5 reductase (heterologous expression; prepared in *Escherichia coli*)

|  | Background | | mSCD1 only | | mSCD1 + cyt b5 | | mSCD1 + cyt b5 reductase | | Complete complex | |
|---|---|---|---|---|---|---|---|---|---|---|
| mSCD1 | – | – | + | + | + | + | + | + | + | + |
| cyt b5 | – | – | – | – | + | + | – | – | + | + |
| cyt b5 reductase | – | – | – | – | – | – | + | – | + | + |
| cpm 18:0-CoA | 27,392 | 27,901 | 28,468 | 29,673 | 26,319 | 21,999 | 27,015 | 27,983 | 25,380 | 21,289 |
| cpm 18:1-CoA | 569 | 562 | 1626 | 1743 | 1684 | 1761 | 1372 | 1513 | 1599 | 2018 |
| total cpm | 37,961 | 28,463 | 30,094 | 31,416 | 28,003 | 23,760 | 28,387 | 29,496 | 26,979 | 23,307 |
| % conversion | 2.03% | 1.97% | 5.40% | 5.55% | 6.01% | 7.41% | 4.83% | 5.13% | 5.93% | 8.66% |
| average conversion | 2.00% | | 5.48% | | 6.71% | | 4.98% | | 7.29% | |
| Correction by subtraction of background | 0.00% | | 3.47% | | 4.71% | | 2.98% | | 5.29% | |
| % change vs. mSCD1 | | | | | 35.64% | | –14.2% | | 52.35% | |

TABLE 4

Comparison of reconstituted complexes of recombinant DesA3 (heterologous expression in *M. smegmatis*) with Rv3230c (heterologous expression; prepared in *Escherichia coli*)[a]

| M. smegmatis fraction used | Total | Soluble | Pellet | Total | Soluble | Pellet | Total | Soluble | Pellet |
|---|---|---|---|---|---|---|---|---|---|
| *E. coli* pQE80 control lysate used | − | − | − | + | + | + | − | − | − |
| *E. coli* pQE80-Rv3230c lysate[b] | − | − | − | − | − | − | + | + | + |
| *M. smegmatis* pVV16 control lacking DesA3[c] | | | | | | | | | |
| %18:0 | 82% | 91% | 86% | 84% | 95% | 91% | 84% | 95% | 93% |
| %18:1 | 6% | 3% | 3% | 4% | 3% | 4% | 4% | 3% | 3% |
| % side product[d] | 12% | 6% | 11% | 12% | 2% | 5% | 12% | 2% | 4% |
| *M. smegmatis* pVV16-DesA3[e] | | | | | | | | | |
| %18:0 | 74% | 91% | 74% | 77% | 94% | 83% | 66% | 83% | 63% |
| %18:1 | 13% | 3% | 4% | 7% | 4% | 9% | 20% | 14% | 28% |
| % side product | 13% | 6% | 22% | 16% | 2% | 8% | 14% | 3% | 9% |
| fold-increase in 18:1[f] | 2.2 | 1.0 | 1.3 | 1.8 | 1.3 | 2.5 | 5.0 | 4.7 | 9.3 |

[a]Samples were analyzed by phosphorimaging as described above.
[b]The subcellular fractions of *M. smegmatis* used in the experiment were: total cell lysate, soluble fraction or pellet fraction prepared as described above.
[c]Control studies using *M. smegmatis* pVV16 not able to express DesA3.
[d]GC/MS analysis of the side product obtained from unlabeled reactions showed this band contained a mixture of 16:0, 16:1 and 18:0 fatty acids, with 16:1 predominant and 16:0 and 18:0 present in trace amounts. Only the 18:0 would be detected by the radiolabeling method. This partial separation of radiolabeled 18:0-CoA from total cellular lipids is observed in other studies.
[e]Desaturase reaction studies using *M. smegmatis* pVV16-DesA3 expressing DesA3.
[f]The fold increase in 18:1 production relative to the comparable control studies.

The inventors cloned, expressed and isolated both DesA3 (Rv3229c) and Rv3230c. The Rv3230c gene is annotated as a putative oxidoreductase in intermediary metabolism. The data presented here demonstrate a function for Rv3230c, as a previously unidentified oxidoreductase function, to the DesA3 complex.

Figure 2:
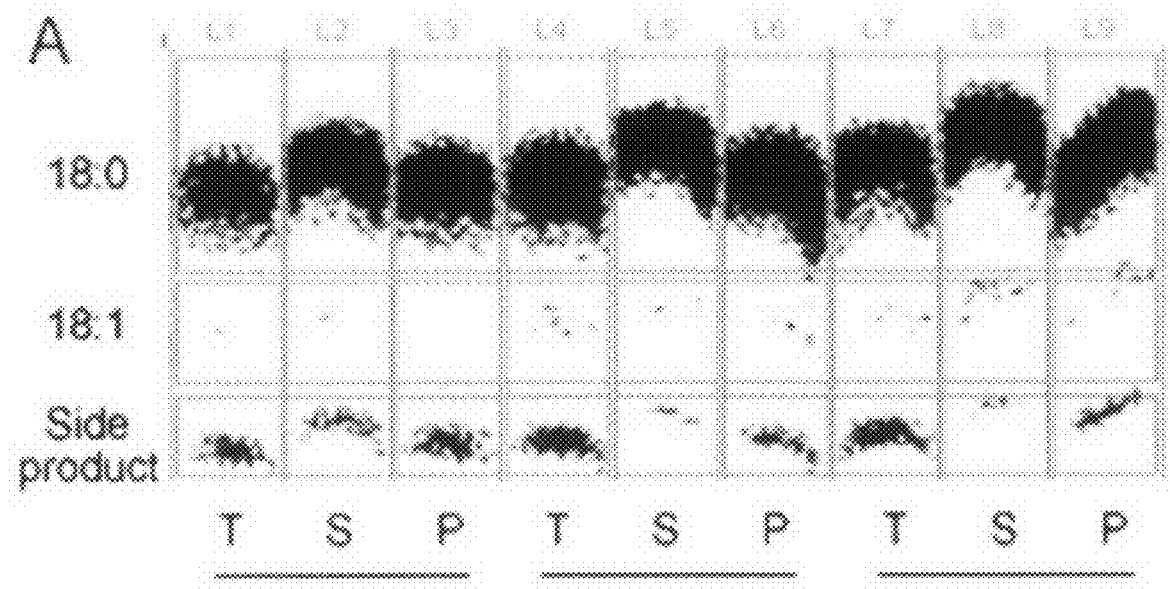
FIG. 2 shows images obtained from a Packard Instant Imager (Packard, Meriden, Conn.) for phosphorescence detection of radioactive decay and quantitative analysis (bottom) of duplicate trials for the conversion of [$^{14}$C]-18:0-CoA to [$^{14}$C]-18:1-CoA after expression of DesA3 from vector DesA3HispVV16 in *Mycobacterium smegmatis*.
Figure 2:
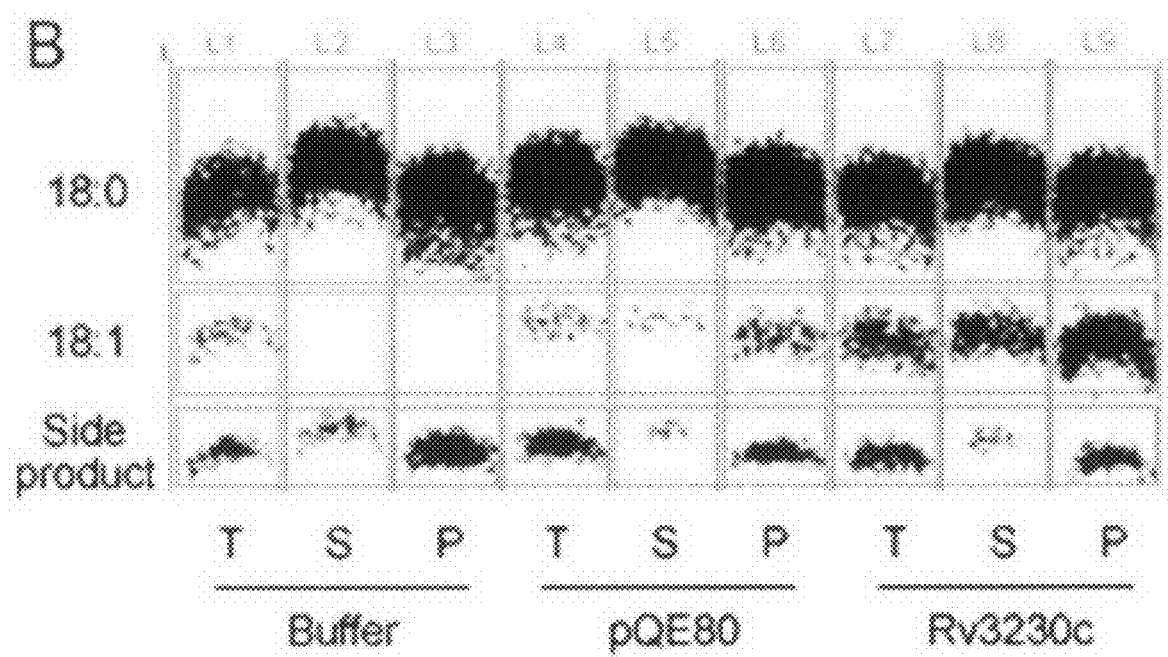

FIG. 2 shows activity assays after expression of DesA3 from vector DesA3HispVV16 in *Mycobacterium smegmatis*. The product 18:1-CoA is indicated. T, S, and P correspond to the total, supernatant, and pellet fractions of *Mycobacterium smegmatis* lysate, respectively. Shown in (A) are data obtained for the control—empty vector pVV16. The upper band is the unreacted substrate, the bottom band is the side reaction product from *Mycobacterium smegmatis* lysate, and the middle band is the oleic acid product, confirmed by standard reaction. Addition of Rv3230c (expressed and partially purified from *Escherichia coli*) gives a 10-fold increase in the rate of production of 18:1-CoA. In different experiments where the amount of Rv3230c is varied, the increase in activity of production of 18:1-CoA is up to 30-fold, indicating the existence of a multi-protein composition for DesA3 activity in *Mycobacterium tuberculosis*. The decrease in activity beyond addition of the optimal amount of Rv3230c is assigned to excess consumption of the cosubstrate NADPH, which is consistent with unbalanced oxidoreductase activity relative to desaturase activity.

It is to be understood that this invention is not limited to the particular devices, methodology, protocols, subjects, or reagents described, and as such may vary. It is also to be understood that the terminology used herein is for the purpose of describing particular embodiments only, and is not intended to limit the scope of the present invention, which is limited only by the claims. Other suitable modifications and adaptations of a variety of conditions and parameters, obvious to those skilled in the art of genetic engineering, molecular biology, and biochemistry, are within the scope of this invention. All publications, patents, and patent applications cited herein are incorporated by reference in their entirety for all purposes.

What is claimed is:

1. An isolated protein comprising an amino acid sequence that is at least 95% identical to the amino acid sequence of SEQ ID NO:9, wherein the protein, when combined with a desaturase, increases desaturation of fatty acids.

2. The isolated protein of claim 1, wherein the protein comprises at least 380 amino acids of SEQ ID NO:9.

3. An isolated protein composition comprising a desaturase from *Mycobacterium tuberculosis* and an oxidoreductase that has at least 95% amino acid sequence identity to the amino acid sequence of SEQ ID NO:9, wherein the protein composition desaturates fatty acids.

4. An isolated protein composition according to claim 3 wherein the desaturase has at least 95% amino acid sequence identity to the amino acid sequence of SEQ ID NO:10.

5. An isolated protein composition according to claim 3 wherein the desaturase is Rv3229c.

6. A method of screening target ligands specific for a desaturase complex, which comprises:
   a) preparing a first mixture containing a desaturase and an oxidoreductase by expressing one or more first genes encoding the desaturase and expressing one or more second genes encoding the oxidoreductase;
   b) contacting the first mixture with a target ligand to form a second mixture;
   c) contacting the second mixture with a fatty acid; and
   d) determining the activity of the desaturase in the presence of the target ligand and comparing that activity with the activity of the desaturase in the absence of the target ligand, wherein the change in activity of the desaturase is correlated with binding of the target ligand to the desaturase complex.

7. The method of claim 6 wherein the desaturase is selected from the group of fatty acid desaturases capable of inserting double bonds into fatty acyl chains derivatized to CoA, glycerols, alkyl ethers, alkenyl ethers, phosphatides, mycolic acids, or glycosidic sugars.

8. The method of claim 7 wherein the desaturase is a stearoyl-CoA desaturase.

9. The method of claim 7 wherein the desaturase has at least 95% amino acid sequence identity to the amino acid sequence of SEQ ID NO:10.

10. The method of claim 7 wherein the desaturase is Rv3229c.

11. The method of claim 6 wherein the oxidoreductase is selected from the group consisting of oxidoreductases that are specific for NADH or NADPH, and that reduce enzyme-bound metal ions including heme groups, iron-sulfur centers and those bound by amino acid side chains such as histidine, glutamate, aspartate, cysteine, or tyrosine.

12. The method of claim 11 wherein the oxidoreductase is a cytochrome b5.

13. The method of claim 11 wherein the oxidoreductase is a cytochrome b5 reductase.

14. The method of claim 11 wherein the oxidoreductase has at least 95% amino acid sequence identity to the amino acid sequence of SEQ ID NO:9.

15. The method of claim 11 wherein the oxidoreductase is Rv3230c.

16. A method of screening target ligands specific for a desaturase complex, which comprises:
   a) preparing a mixture containing a desaturase, an oxidoreductase, a fatty acid, and optionally a target ligand; and b) determining the activity of the desaturase in the presence of the target ligand and comparing that activity with the activity of the desaturase in the absence of the target ligand, wherein the change in activity of the desaturase is correlated with binding of the target ligand to the desaturase complex.

17. The method of claim 16 wherein the desaturase is a stearoyl-CoA desaturase.

18. The method of claim 16 wherein the oxidoreductase is a cytochrome b5.

19. The method of claim 16 wherein the oxidoreductase is a cytochrome b5 reductase.

* * * * *